United States Patent [19]

Boesch

[11] 4,150,142

[45] Apr. 17, 1979

[54] DERIVATIVES OF ALKOXY-5-PHENYL-3 OXADIAZOLINE-1,3,4 ONE-2, THEIR PREPARATION AND INSECTICIDAL AND ACARICIDAL COMPOSITIONS WHICH CONTAIN THEM

[75] Inventor: Roger Boesch, Vitry-sur-Seine, France

[73] Assignee: Philagro S.A., Lyon, France

[21] Appl. No.: 651,783

[22] Filed: Jan. 23, 1976

[30] Foreign Application Priority Data

Feb. 3, 1975 [FR] France .............................. 75 03282

[51] Int. Cl.$^2$ ..................... C07D 271/10; A01N 9/22
[52] U.S. Cl. .............................. 424/272; 260/307 A; 260/569; 560/9; 560/24; 560/25; 560/29
[58] Field of Search ..................... 260/307 A; 424/272

[56] References Cited

U.S. PATENT DOCUMENTS

| 3,184,470 | 5/1965 | Ruschig et al. ..................... 260/308 |
| 4,076,824 | 2/1978 | Boesch ................................. 424/272 |

FOREIGN PATENT DOCUMENTS

58140 8/1973 Japan.

OTHER PUBLICATIONS

Wiley–"Chemistry of Heterocyclic Compounds"–vol. 17–(1962)–Interscience Publishers–pp. 274–277.

*Primary Examiner*—Raymond V. Rush
*Attorney, Agent, or Firm*—Browdy and Neimark

[57] ABSTRACT

The invention pertains to certain oxadiazolinones of the formula:

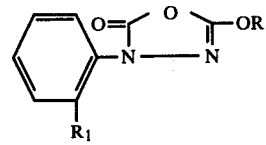

in which R represents an alkyl radical containing 1 to 4 carbon atoms and $R_1$ represents an alkyl radical containing 2 to 4 carbon atoms, an alkoxy radical of which the alkyl part contains 1 to 4 carbon atoms, an alkylthio radical of which the alkyl part contains 1 to 4 carbon atoms, or trifluoromethyl, and to their preparation and the compositions in which they are present, which compounds and compositions have utility as nematocides, acaricides and insecticides.

10 Claims, No Drawings

DERIVATIVES OF ALKOXY-5-PHENYL-3 OXADIAZOLINE-1,3,4 ONE-2, THEIR PREPARATION AND INSECTICIDAL AND ACARICIDAL COMPOSITIONS WHICH CONTAIN THEM

The present invention relates to new derivatives of oxadiazolinone of the general formula:

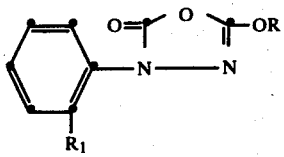
(I)

in which R represents an alkyl radical containing 1 to 4 carbon atoms and $R_1$ represents an alkyl radical containing 2 to 4 carbon atoms, an alkoxy radical of which the alkyl part contains 1 to 4 carbon atoms, an alkylthio radical of which the alkyl part contains 1 to 4 carbon atoms, or trifluoromethyl, and to their preparation and the compositions in which they are present.

The products of the general formula (I) in which R and $R_1$ are defined as above can be obtained by the action of phosgene on a product of the general formula:

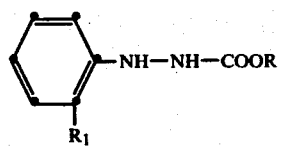
(II)

in which R and $R_1$ are defined as above, followed by cyclisation, in a basic medium, of the intermediate compound obtained, of the general formula:

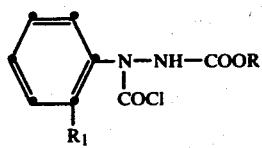
(III)

in which R and $R_1$ are defined as above.

The reaction with phosgene is generally carried out by heating in an organic solvent such as toluene, at the reflux temperature of the reaction mixture.

The cyclisation of the product of the general formula (III) is carried out in the presence of a base such as triethylamine, sodium hydroxide or ammonia in an organic solvent such as methylene chloride.

The products of the general formula (II) can be prepared by the action of a product of the general formula:

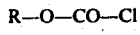
R—O—CO—Cl     (IV)

in which R is defined as above, on a phenylhydrazine of the general formula:

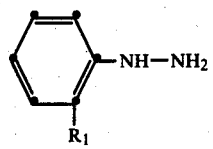
(V)

in which $R_1$ is defined as above.

The reaction is generally carried out in a solvent such as pyridine.

The new products of the general formula (I) have remarkable insecticidal and acaricidal properties. They are particularly active by contact and by ingestion. Interesting results are obtained on diptera, coleoptera, lepidoptera, hemiptera and orthoptera.

The compounds are also excellent soil insecticides.

The new products of the general formula (I) also have a remarkable nematocide activity. More particularly, they prove active, in vivo, against Ditylenchus dipsaci at doses of between 10 and 100 kg/ha and they are preferably used by treating soil by powdering, or in the form of granules.

The present invention also relates to the insecticidal, acaricidal and nematocide compositions which are used in agriculture and contain, as the active product, at least one derivative of the general formula (I) combined with one or more carriers or adjuvants which are compatible with the active product or products and suitable for use in agriculture. These compositions can contain other compatible pesticides such as fungicides.

Furthermore, the activity of the products of the general formula (I) is very markedly improved if they are combined with a synergistic agent. The synergistic agents which are particularly suitable are nitrobenzene derivatives and more especially 2-propargyloxy-nitrobenzene or 2-propargyloxy-5-chloro-nitrobenzene.

The present invention also relates to the insecticidal and acaricidal compositions in which a product of the general formula (I) is combined with a synergistic agent.

In general, the best results are obtained with compositions which contain two parts (by weight) of a nitrobenzene derivative and one part (by weight) of a product of the general formula (I).

It is already known from Japanese Application 48/58,140 that certain 3-(alkoxy- or phenoxy-phenyl)-1,3,4-oxadiazolin-2-ones, optionally substituted in the phenyl nucleus by one or two methyl radicals or halogen atoms, are active against certain insects and/or acarides. However, it has now been found that the compounds according to the invention, in the formula of which the phenyl nucleus carries only one substituent, as defined above, this substituent being in the 2-position, are less phytotoxic and more active.

The examples which follow and are given without implying a limitation, illustrate the present invention.

EXAMPLE 1

Methyl 3-(2-methoxy-phenyl)-carbazinate (196 g.) is added to a 14.8% strength (weight/volume) solution of phosgene in toluene (1,000 cc.). The solution obtained is then heated gradually until the evolution of gas ceases, whilst the condensable vapors are condensed by means of a condenser using solid carbon dioxide. The temperature of the reaction mixture is at that stage 90° C. The solid carbon dioxide condenser is replaced by a coil condenser and the mixture is heated under reflux until the evolution of gas has ceased. After cooling to 5° C., the precipitate formed is filtered off and then dried under reduced pressure (0.5 mm Hg) at 20° C.; methyl 3-(2-methoxy-phenyl)-3-chlorocarbonyl-carbazinate (258.5 g.) melting at 139° C. is obtained. This product is suspended in methylene chloride (1,000 cc.) and triethylamine (140 cc.) is then added. The solution thus obtained gradually produces a precipitate of triethylamine hydrochloride. After stirring for 3 hours at 20° C., water (250 cc.) is added to dissolve the hydrochloride precipitate. The methylene chloride solution is separated off by decantation and then washed successively with normal hydrochloric acid (250 cc.) and with water (twice 250 cc.). After drying over sodium sulphate, the solvent is removed by evaporation under reduced pressure (20 mm Hg) at 50° C. The residual solid is recrystallised from isopropanol (732 cc.). This gives 5-methoxy-3-(2-methoxy-phenyl)-1,3,4-oxadiazolin-2-one (170.6 g.) melting at 77° C.

The methyl 3-(2-methoxy-phenyl)-carbazinate starting material (melting point=102° C.) can be prepared by the action of methyl chloroformate on 2-methoxyphenylhydrazine hydrochloride in pyridine.

The following products are prepared by following the procedure of Example 1 but starting from suitable starting materials:

| Example No. | R | $R_1$ | Melting point (m.p.) or freezing point (f.p.) (°C.) |
|---|---|---|---|
| 2 | $-C_2H_5$ | $CH_3O-$ | m.p. = 60° |
| 3 | $-(CH_2)_2CH_3$ | $CH_3O-$ | f.p. = 32° |
| 4 | $-CH(CH_3)_2$ | $CH_3O-$ | m.p. = 63° |
| 5 | $-CH_3$ | $C_2H_5O$ | m.p. = 66° |
| 6 | $-CH_3$ | $(CH_3)_2CHO-$ | Oil |
| 7 | $-CH_3$ | $C_2H_5-$ | m.p. = 53° |
| 8 | $-C_2H_5$ | $C_2H_5-$ | f.p. = 35° |
| 9 | $-CH_3$ | $F_3C-$ | m.p. = 84° |
| 10 | $-C_2H_5$ | $F_3C-$ | m.p. = 57° |
| 11 | $-CH(CH_3)_2$ | $F_3C-$ | m.p. = 74° |
| 12 | $-(CH_2)_2CH_3$ | $F_3C-$ | m.p. = 58° |
| 13 | $-(CH_3)_3CH_3$ | $F_3C-$ | f.p. = 28° |
| 14 | $-CH_3$ | $CH_3S-$ | m.p. = 81° |
| 15 | $-C_2H_5$ | $CH_3S-$ | m.p. = 79° |
| 16 | $-C_2H_5$ | $(CH_3)_2CHO-$ | Oil |
| 17 | $-CH(CH_3)_2$ | $(CH_3)_2CHO-$ | Oil |
| 18 | $-CH_3$ | $C_2H_5S-$ | m.p. = 66° |

EXAMPLE 19

A condensation product (10 parts) of octylphenol and ethylene oxide in the ratio of 10 molecules of ethylene oxide per molecule of octylphenol is added to a solution (25 parts) of 5-methoxy-3-(2-methoxy-phenyl)-1,3,4-oxadiazolin-2-one in a mixture (65 parts) of equal parts of toluene and acetophenone. The solution obtained is used after dilution with water in the ratio of 200 cc. of this solution per 100 liters of water.

EXAMPLE 20

A condensation product (10 parts) of octylphenol and ethylene oxide in the ratio of 10 molecules of ethylene oxide per molecule of octylphenol is added to a solution of a mixture (25 parts) of 2-propargyloxy-nitrobenzene and 5-methoxy-3-(2-methyl-thio-phenyl)-1,3,4-oxadiazolin-2-one (2 parts: 1 part by weight) in a mixture (65 parts) of equal parts of toluene and acetophenone. The solution obtained is used, after dilution with water, in the ratio of 200 cc. of this solution per 100 liters of water.

The insecticidal, acaricidal and nematicidal activities can be demonstrated by the following tests.

EXAMPLE 21

(a) Insecticidal activity through contact (fly, tribolium)

An acetone solution (1 cc.) of the product to be studied, at a given concentration, is sprayed into a 120 cc. glass pot. When the solvent has evaporated, the insects (5 flies or 10 triboliums) are placed in the pots, which are covered with a metal gauze. The number of dead insects after 24 hours' contact, in the case of the flies, and after 3 days' contact, in the case of the triboliums, is counted. The concentration which causes the death of 90% of the insects is determined.

| Product of Example | Fly | Tribolium |
|---|---|---|
| 1 | $10^{-5}$ | $2 \times 10^{-6}$ |
| 2 | $10^{-4}$ | $2 \times 10^{-6}$ |
| 3 | $2 \times 10^{-5}$ | $6 \times 10^{-6}$ |
| 4 | $4 \times 10^{-5}$ | $2 \times 10^{-6}$ |
| 5 | $3 \times 10^{-5}$ | $2 \times 10^{-5}$ |
| 6 | $3 \times 10^{-5}$ | $2 \times 10^{-5}$ |
| 7 | $2 \times 10^{-5}$ | $2 \times 10^{-5}$ |
| 8 | $8 \times 10^{-5}$ | $\leq 10^{-5}$ |
| 9 | $10^{-5}$ | $8 \times 10^{-6}$ |
| 10 | $10^{-5}$ | $8 \times 10^{-6}$ |
| 11 | $10^{-3}$ | $3 \times 10^{-5}$ |
| 12 | $10^{-4}$ | $10^{-5}$ |
| 13 | $5 \times 10^{-5}$ | $6 \times 10^{-5}$ |
| 14 | $10^{-3}$ | $10^{-5}$ |
| 15 | | $2 \times 10^{-6}$ |
| 16 | $10^{-4}$ | $10^{-3}$ |
| 17 | $10^{-3}$ | $10^{-3}$ |
| 18 | $3 \times 10^{-5}$ | $3 \times 10^{-6}$ |

If compound 8 and the analogous compound of the cited patent (compound 2), namely 5-ethoxy-3-(2-methyl-phenyl)-1,3,4-oxadiazolin-2-one (compound A) are respectively tested with flies, as described above, it is found that the death of 90% of the insects results at a concentration of $3 \times 10^{-4}$ of the known compound and at a concentration of only $8 \times 10^{-5}$ of the compound according to the invention.

(b) Insecticidal activity through contact; [topical treatment of insects (fly, cricket)]

A known quantity of an aqueous acetone solution of the product to be studied is deposited with a micrometer syringe of the "Agla" type or of the "Hamilton" type on the prothorax of each insect, the amount being 0.001 cc. per fly or 0.003 cc. per cricket. The insects are anaesthetised with carbon dioxide. Various concentrations are used. The mortality is evaluated 24 hours after the treatment in the case of the flies and three days after the treatment in the case of the crickets. The concentration which causes 50% mortality is determined.

| Product of Example | Fly | Cricket |
|---|---|---|
| 1 | $2 \times 10^{-3}$ | $3 \times 10^{-4}$ |
| 2 | | $3 \times 10^{-3}$ |
| 4 | $10^{-3}$ | $10^{-3}$ |
| 6 | | $10^{-3}$ |
| 10 | $8 \times 10^{-4}$ | |
| 11 | $6 \times 10^{-4}$ | |
| 14 | | $10^{-3}$ |

EXAMPLE 22

Insecticidal activity through contact-ingestion (foliage treated by dipping; caterpillars of *Plutella maculipennis* and caterpillars of *Pieris brassicae*)

Young cabbage leaves are dipped for 10 seconds in the solutions to be studied. When they are dried, they are infested with caterpillars (3rd stage) of *Plutella maculipennis* or *Pieris brassicae*. The mortality is determined 3 days after the treatment. The concentration which results in 90% mortality of the caterpillars is determined.

| Product of Example | Plutella | Pieris |
|---|---|---|
| 1 | $8 \times 10^{-5}$ | $8 \times 10^{-5}$ |
| 2 | $4 \times 10^{-4}$ | $2 \times 10^{-4}$ |
| 3 | $8 \times 10^{-4}$ | $3 \times 10^{-4}$ |
| 4 | $2 \times 10^{-4}$ | $10^{-4}$ |
| 5 | $10^{-4}$ | $3 \times 10^{-4}$ |
| 6 | $10^{-4}$ | $2.5 \times 10^{-4}$ |
| 7 | $5 \times 10^{-5}$ | $10^{-4}$ |
| 8 | $6 \times 10^{-5}$ | $3 \times 10^{-4}$ |
| 9 | Less than $10^{-4}$ | $3 \times 10^{-4}$ |
| 10 | Less than $10^{-4}$ | $3 \times 10^{-4}$ |
| 11 | $10^{-4}$ | $10^{-4}$ |
| 12 | $2 \times 10^{-4}$ | |
| 13 | $10^{-3}$ | |
| 14 | $5 \times 10^{-4}$ | $10^{-3}$ |
| 16 | $5 \times 10^{-4}$ | $10^{-3}$ |
| 17 | $5 \times 10^{-4}$ | $2 \times 10^{-4}$ |
| 18 | $10^{-4}$ | $10^{-4}$ |

EXAMPLE 23

Acaricidal activity by contact-ingestion (foliage treated by dipping; *Tetranychus telarius*, parthenogenetic females)

Leaves of bean plants at the cotyledon leaf stage are dipped for 10 seconds in the solution of the product to be studied. After drying, they are infested from leaves of heavily contaminated bean plants. The contaminated bean plants are kept alive by immersing the roots and the base of the stem in distilled water. The mortality is determined 2 to 4 days after contamination. The concentration which results in 90% mortality of the acarides is determined.

| Product of Example | Tetranychus telarius |
|---|---|
| 1 | $10^{-3}$ |
| 2 | $10^{-3}$ |
| 3 | $10^{-3}$ |
| 4 | $8 \times 10^{-4}$ |
| 9 | $10^{-3}$ |
| 10 | $10^{-3}$ |

EXAMPLE 24

Acaricidal-ovicidal activity through contact 100 mm diameter discs are taken from bean leaves infested with Tetranychus telarius. The discs carrying 30 to 100 parthenogenetic eggs are immersed for 10 seconds in the solution of the product to be studied and are then fixed to a glass plate. Each disc is surrounded by a 3 to 5 mm wide vaseline ring at a distance of about 5 mm from the periphery of the disc. The number N of intact eggs is counted under a magnifying glass. The plates are kept at 25° C. for 7 days. The hexapod larvae immobilised in the ring of vaseline (n) are counted. The concentration ($LC_{90}$) resulting in 90% mortality of the eggs (% of eggs killed $=(N-n)/N \times 100$) is determined.

| Product of Example | Tetranychus telarius |
|---|---|
| 1 | $5 \times 10^{-4}$ |
| 2 | $5 \times 10^{-4}$ |
| 3 | $1.5 \times 10^{-4}$ |
| 4 | $2 \times 10^{-4}$ |
| 5 | Less than $10^{-3}$ |
| 6 | Less than $10^{-3}$ |
| 7 | Less than $10^{-3}$ |
| 9 | $2 \times 10^{-4}$ |
| 10 | $3 \times 10^{-4}$ |
| 11 | $10^{-4}$ |
| 12 | $10^{-4}$ |
| 13 | $5 \times 10^{-4}$ |
| 16 | $<10^{-3}$ |
| 18 | $<10^{-3}$ |

EXAMPLE 25

Combination with 2-propargyloxy-nitrobenzene (A) and 2-propargyloxy-5-chloro-nitrobenzene (B)

(a) Insecticidal activity through contact (fly, tribolium)

The concentration which causes the death of 90% of the insects is determined.

| Product of Example | Without synergistic agent | | Combination of the product (1 part) with B (2 parts) | |
|---|---|---|---|---|
| | Fly | Tribolium | Fly | Tribolium |
| 1 | $10^{-5}$ | $2 \times 10^{-6}$ | $3 \times 10^{-7}$ | $2 \times 10^{-7}$ |
| 4 | $4 \times 10^{-5}$ | $2 \times 10^{-6}$ | $5 \times 10^{-7}$ | $8 \times 10^{-7}$ |
| 8 | $8 \times 10^{-5}$ | $\leq 10^{-5}$ | $3 \times 10^{-6}$ | $3 \times 10^{-6}$ |
| 11 | $10^{-3}$ | $3 \times 10^{-5}$ | $5 \times 10^{-6}$ | $8 \times 10^{-6}$ |
| 14 | | $2 \times 10^{-6}$ | $2 \times 10^{-6}$ | $5 \times 10^{-7}$ |

(b) Insecticidal activity through contact [topical treatment of the insects (fly, cricket)].

| Concentration of the product of Example 1 | Concentration of product A | Concentration of product B | Fly % Mortality | Cricket % Mortality |
|---|---|---|---|---|
| $5 \times 10^{-5}$ | 0 | 0 | 0 | 0 |
| $5 \times 10^{-5}$ | $5 \times 10^{-5}$ | 0 | 5 | 0 |
| $5 \times 10^{-5}$ | $10^{-4}$ | 0 | 10 | 0 |
| $5 \times 10^{-5}$ | 0 | $5 \times 10^{-5}$ | 30 | 0 |
| $5 \times 10^{-5}$ | 0 | $10^{-4}$ | 40 | 0 |
| $10^{-4}$ | 0 | 0 | 10 | 0 |
| $10^{-4}$ | $10^{-4}$ | 0 | 75 | 10 |
| $10^{-4}$ | $2 \times 10^{-4}$ | 0 | 80 | 30 |
| $10^{-4}$ | 0 | $10^{-4}$ | 100 | 30 |
| $10^{-4}$ | 0 | $2 \times 10^{-4}$ | 100 | 30 |
| $2 \times 10^{-4}$ | 0 | 0 | 0 | 50 |
| $2 \times 10^{-4}$ | $2 \times 10^{-4}$ | 0 | 100 | 90 |
| $2 \times 10^{-4}$ | $4 \times 10^{-4}$ | 0 | 100 | 100 |
| $2 \times 10^{-4}$ | 0 | $2 \times 10^{-4}$ | 100 | 70 |
| $2 \times 10^{-4}$ | 0 | $4 \times 10^{-4}$ | 100 | 100 |

(c) Insecticidal activity through contact-ingestion (foliage treated by dipping; caterpillars of *Plutella Maculipennis* and caterpillars of *Pieris brassicae*).

| Concentration of the product of Example 1 | Concentration of the product B | Plutella % mortality | Pieris % mortality |
|---|---|---|---|
| $3 \times 10^{-6}$ | 0 | 10 | 0 |
| $3 \times 10^{-6}$ | $6 \times 10^{-6}$ | 0 | 0 |
| $10^{-5}$ | 0 | 10 | 0 |
| $10^{-5}$ | $2 \times 10^{-5}$ | 30 | 10 |
| $3 \times 10^{-5}$ | 0 | 50 | 0 |
| $3 \times 10^{-5}$ | $6 \times 10^{-5}$ | 95 | 75 |
| $10^{-4}$ | 0 | 100 | 100 |
| $10^{-4}$ | $2 \times 10^{-4}$ | 100 | 100 |
| $3 \times 10^{-4}$ | 0 | 100 | 100 |
| $3 \times 10^{-4}$ | $6 \times 10^{-4}$ | 100 | 100 |
| $10^{-3}$ | 0 | 100 | 100 |
| $10^{-3}$ | $2 \times 10^{-3}$ | 100 | 100 |

EXAMPLE 26

The applicant company has also found, in field experiments with two compositions, namely a wettable powder containing 50% of active material, and an emulsifiable concentrate containing 200 g of active material/l, that the compound No. 1 is equally active, that is to say it completely controls various insects of the aphid family, at a dose of 40 g of active material/hl, especially the bean aphid (*Aphis fabae*), the cherry black-fly (*Myzus cerasi*) the rosy apple aphid (*Dysaphis plantaginea*), the cabbage aphid (*Brevicoryne brassicae*), the rose aphid (*Macrosiphym rosae*) and the wheat aphid (*Sitobium sp.*) Furthermore, at a dose of 60 g of active material/hl, it controls pear psylla (*Psylla piricola*) at the young larvae stage.

It should be noted that at the use doses, the selectivity as regards the host cultures of the treated parasites is good.

EXAMPLE 27

Insecticidal activity through contact-ingestion in a greenhouse

Plants of broccoli (*Brassica olearacea*) at the four-leaf stage, grown in shallow pots, are treated by spraying with a 25% strength emulsifiable solution of the product to be studied. The treated plants are allowed to dry and thereafter leaves are taken from each and distributed in cylindrical boxes of ten caterpillars (3rd stage) per box, respectively, of *Plutella maculipennis* and *Pieris brassicae*. After a few hours (series 0) the dead insects are counted. In another series, the count is made (series +2) two days after the treatment. The experiments are each repeated twice per experiment (sic) and per concentration, respectively using compound A referred to above and compounds 8 and 1. The results, expressed as a percentage mortality of the caterpillars, are shown in the table which follows:

| Compound | Dose in mg/hl | Plutella maculipennis 0 | +2 | Pieris brassicae 0 | +2 |
|---|---|---|---|---|---|
| A | 25 | 50 | 25 | 15 | 0 |
|   | 50 | 75 | 35 | 20 | 0 |
| 8 | 25 | 100 | 60 | 80 | 60 |
|   | 50 | 100 | 40 | 100 | 80 |
| 1 | 25 | 100 | 80 | 100 | 80 |
|   | 50 | 100 | 100 | 100 | 100 |

This example shows clearly the markedly superior activity of the products of the invention compared to the closest known homologue, both from the point of view of immediate effect and of persistence of the effect.

The compositions according to the invention, wherein the content of active material can be between 0.05 and 80% by weight, usually contain at least one carrier and/or at least one surface-active agent in addition to the active material according to the invention.

The term "carrier" in the sense of the present description denotes an organic or inorganic, natural or synthetic material with which the active material is combined so as to facilitate its application to the plant, to seeds or to the soil, or to facilitate its transport or its handling. The carrier can be solid (clays, natural silicates—such as talc—or synthetic silicates, calcined magnesia, kieselguhr, tricalcium phosphate, cork powder, absorbent charcoal, resins, waxes, solid fertilisers and the like) or fluid (water, alcohols, ketones, petroleum fractions, chlorinated hydrocarbons or liquefied gases).

The surface-active agent can be en emulsifying agent, dispersing agent or wetting agent, which can be ionic or non-ionic. Examples which may be mentioned are salts of polyacrylic acids and of ligninsulphonic acids, sulphoricinoleates, quaternary ammonium salts, condensates of ethylene oxide with fatty alcohols, fatty acids or fatty amines and especially products based on condensates of ethylene oxide such as condensates of ethylene oxide with octylphenol, or fatty acid esters of anhydrosorbitols which have been solubilised by etherification of the free hydroxyl radicals by condensation with ethylene oxide. It is preferable to use agents of the non-ionic type, because they are not sensitive to electrolytes.

The compositions according to the invention can be prepared in the form of wettable powders, sprinkling powders, granules, solutions, emulsifiable concentrates, emulsions, suspension concentrates and aerosols.

The wettable powders according to the invention can be prepared so that they contain from 20 to 95% by weight of active material, and they usually contain from 3 to 10% by weight of a dispersing agent and, where necessary, from 0 to 10% by weight of one or more stabilisers and/or other adjuvants, such as penetrating agents, adhesives or anti-caking agents, dyestuffs and the like.

By way of example, the composition of a wettable powder is given below, the percentages being expressed by weight:

| | |
|---|---|
| active material | 50% |
| calcium lignosulphate (deflocculating agent) | 5% |
| isopropylnaphthalene sulphonate (wetting agent) | 1% |
| anti-caking silica | 5% |
| kaolin filler | 39% |

The powders for the treatment of seed or for powdering are usually prepared in the form of a dust concentrate having a similar composition to that of a wettable powder, but without a dispersing agent; they can be diluted on site with a supplementary amount of fluid carrier so that a composition is obtained which can easily coat the seeds to be treated and usually contains from 0.5 to 10% by weight of active material.

By way of example, the composition of a powder for the treatment of seed is given below:

| | |
|---|---|
| active material | 50% |
| anionic wetting agent | 1% |
| anti-caking silica | 6% |
| kaolin (filler) | 43% |

The granules intended to be deposited on the soil are usually prepared so that their dimensions are between 0.1 and 2 mm; they can be manufactured by agglomeration or impregnation. In general, the granules will contain from 0.5 to 25% of active material and from 0 to 10% by weight of additives, such as stabilisers, slow-release modifiers, binders and solvents.

The emulsifiable concentrates which can be applied by spraying usually contain, in addition to the solvent and, where necessary, a co-solvent, from 10 to 50% (by weight/volume) of active material and from 2 to 20% (by weight/volume) of suitable additives, such as stabilisers, penetrating agents, corrosion inhibitors, dyestuffs and adhesives.

By way of example, the composition of an emulsifiable concentrate is given below, the quantities being expressed in g/liter.

| | |
|---|---|
| Active material | 400 g/l |
| dodecylbenzenesulphonate | 24 g/l |
| nonylphenol oxyethylated with 10 molecules (of ethylene oxide) | 16 g/l |
| cyclohexanone | 200 g/l |
| aromatic solvent | q.s.p. 1 litre |

Aqueous dispersions and emulsions, for example compositions obtained by diluting a wettable powder or an emulsifiable concentrate, according to the invention, by means of water, are comprised within the general scope of the present invention. These emulsions can be of the water-in-oil type or of the oil-in-water type and can have a thick consistency such as that of a "mayonnaise".

For a so-called "ultra-low volume" application, with spraying in very fine droplets, solutions in organic solvents, containing from 70 to 99% of active material, are prepared.

The compositions according to the invention can contain other ingredients, for example protective colloids, adhesives or thickeners, thixotropic agents, stabilisers or sequestering agents as well as other known active materials having pesticidal properties, in particular insecticides or fungicides.

I claim:

1. A compound of the formula:

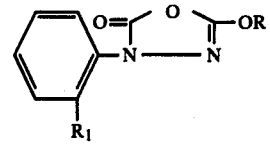

in which:
R represents an alkyl radical containing from 1 to 4 carbon atoms, and
$R_1$ represents an alkoxy or alkylthio radical of which the alkyl part contains 1–4 carbon atoms.

2. A compound in accordance with claim 1, wherein $R_1$ is alkoxy having 1–4 carbon atoms in the alkyl part.

3. A compound according to claim 1, wherein $R_1$ is ethoxy.

4. A compound according to claim 1, wherein $R_1$ is methoxy.

5. A compound in accordance with claim 1 selected from the group consisting of 5-methoxy-3-(2-methoxyphenyl)-1,3,4-oxadiazolin-2-one, 5-methoxy-3-(2-ethoxy-phenyl)-1,3,4-oxadiazolin-2-one, 5-(n-propoxy)-3-(2-methoxy-phenyl)-1,3,4-oxadiazolin-2-one, and 5-isopropoxy-3-(2-methoxy-phenyl)-1,3,4-oxadiazolin-2-one.

6. A compound according to claim 5 comprising 5-(n-propoxy)-3-(2-methoxy-phenyl)-1,3,4-oxadiazolin-2-one.

7. A compound according to claim 5 comprising 5-isopropoxy-3-(2-methoxy-phenyl)-1,3,4-oxadiazolin-2-one.

8. A compound according to claim 5, characterised in that it is 5-methoxy-3-(2-methoxy-phenyl)-1,3,4-oxadiazolin-2-one.

9. A compound according to claim 5, characterised in that it is 5-methoxy-3-(2-ethoxy-phenyl)-1,3,4-oxadiazolin-2-one.

10. Insecticidal, acaricidal and nematocidal composition, characterised in that it contains, as the active material, an effective amount of a compound according to claim 1, in association with one or more compatible diluents or adjuvants which can be used in agriculture.

* * * * *